(12) United States Patent
May et al.

(10) Patent No.: US 8,372,080 B2
(45) Date of Patent: Feb. 12, 2013

(54) TRANS-CUT SLOT ADJUSTMENT MECHANISM

(75) Inventors: Justin J. May, Leesburg, IN (US); Jason Detweiler, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 1072 days.

(21) Appl. No.: 12/198,184

(22) Filed: Aug. 26, 2008

(65) Prior Publication Data
US 2010/0057090 A1    Mar. 4, 2010

(51) Int. Cl.
  *A61B 17/58*   (2006.01)
  *A61B 17/60*   (2006.01)
  *A61F 2/00*    (2006.01)
(52) U.S. Cl. ............................... 606/88; 606/87
(58) Field of Classification Search ............... 606/88–90
    See application file for complete search history.

(56) References Cited

U.S. PATENT DOCUMENTS

| | | | |
|---|---|---|---|
| 4,566,448 A * | 1/1986 | Rohr, Jr. ................ | 606/88 |
| 2004/0249385 A1 | 12/2004 | Faoro | |
| 2005/0143746 A1 | 6/2005 | Steffensmeier et al. | |
| 2006/0336257 | 2/2006 | Steffensmeier | |
| 2006/0155293 A1 | 7/2006 | McGinley et al. | |
| 2006/0155294 A1 | 7/2006 | Steffensmeier et al. | |
| 2006/0217734 A1 | 9/2006 | Sanford et al. | |
| 2006/0293681 A1 | 12/2006 | Claypool et al. | |
| 2007/0005073 A1 | 1/2007 | Claypool et al. | |
| 2007/0173850 A1 | 7/2007 | Rangaiah et al. | |
| 2007/0173854 A1 | 7/2007 | Berger et al. | |
| 2007/0186738 A1 | 8/2007 | McGinley et al. | |
| 2008/0140081 A1 | 6/2008 | Heavener | |

OTHER PUBLICATIONS

Wikipedia—definition of and information on Worm drive, last modified on Aug. 16, 2008.
Wikipedia—definition of and information on Rack and pinion, last modified on Jun. 11, 2008.

* cited by examiner

*Primary Examiner* — Andrew Yang
(74) *Attorney, Agent, or Firm* — Schwegman, Lundberg & Woessner, P.A.

(57) ABSTRACT

An adjustable cut guide and a method of using the adjustable cut guide are disclosed herein. The adjustable cut guide has a guide surface disposed between an actuation mechanism and a base of the adjustable cut guide. The adjustable cut guide also has an adjustment mechanism for adjusting the distance between the guide surface and the base. The actuation mechanism may comprise an adjustment member having an engaged position and a disengaged position. In the engaged position, the adjustment member traverses the guide surface. The adjustment member may include a drive end for mating with, and actuating, the adjustment mechanism when the adjustment member is in the engaged position.

19 Claims, 14 Drawing Sheets

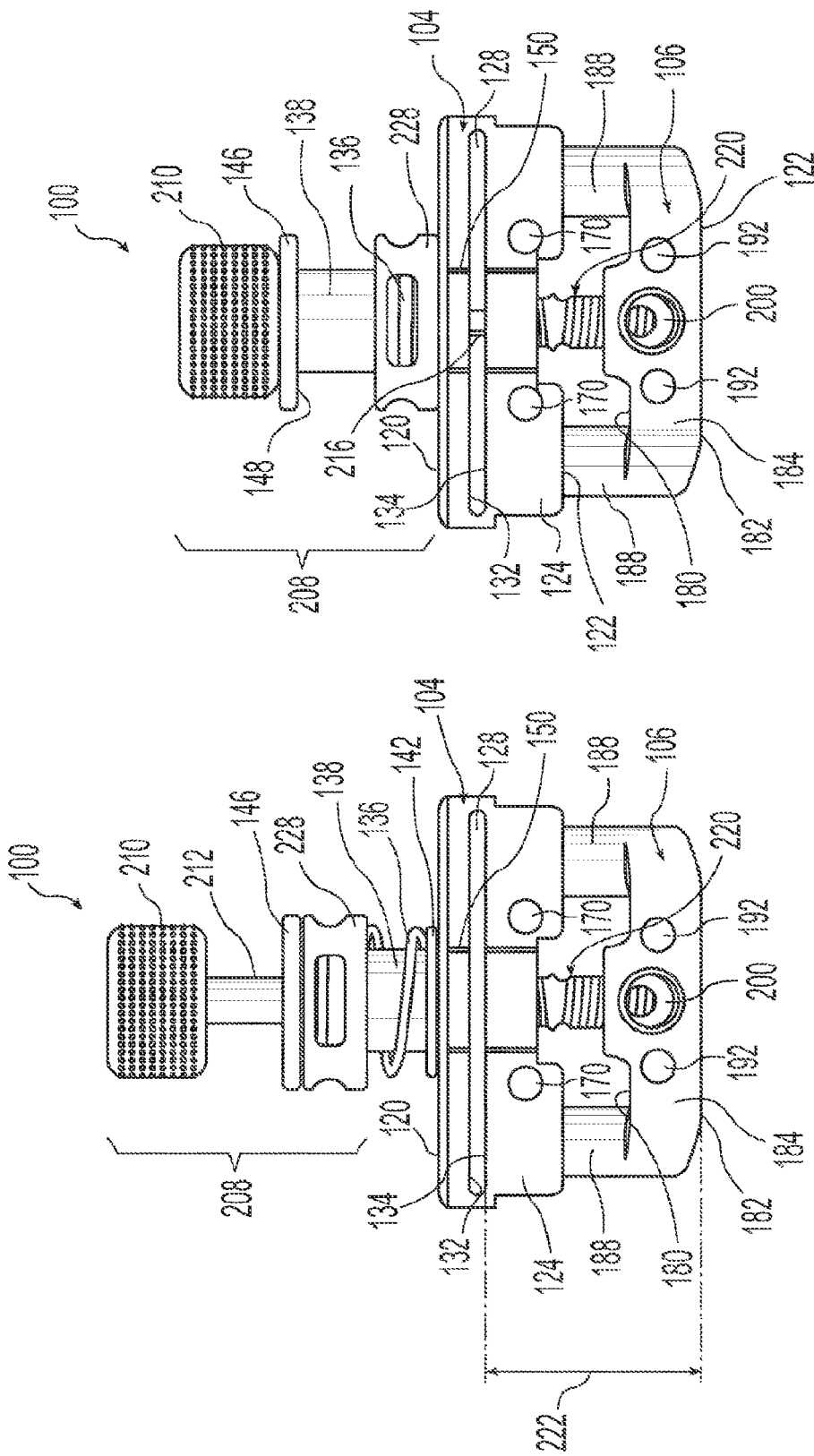

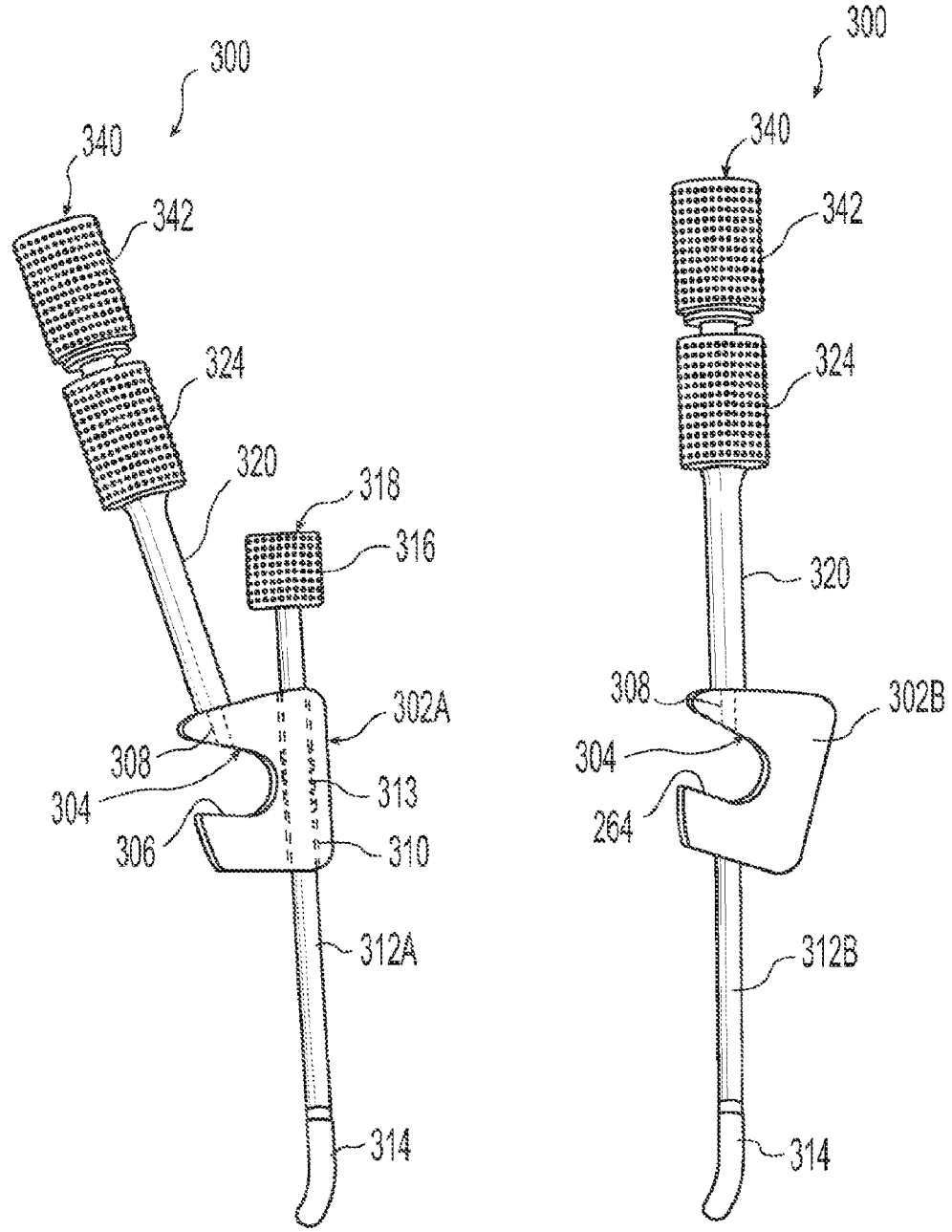

TRANS-CUT SLOT ADJUSTMENT MECHANISM

FIELD OF THE APPLICATION

The present disclosure relates to a method and device for performing arthroplasty. More particularly, the present disclosure relates to an adjustable cut guide for performing arthroplasty.

BACKGROUND

It has long been an object of arthroplasty to minimize the extent to which soft tissue is cut or otherwise damaged or disrupted. In the case of total knee arthroplasty, significant cutting must be performed at the proximal end of the tibia and the distal end of the femur. The procedures involve significant cutting of soft tissue including muscles, tendons and ligaments. Less invasive instruments and procedures using such instruments are desirable to reduce recovery times for patients.

Some procedures may be performed while a joint is extended. In a patello-femoral joint procedure, for example, tibiofemoral extension creates laxity in the extensor mechanism which allows the patella to be subluxed laterally to increase visibility of the femoral anterior compartment. It is desirable in such procedures to utilize cut guides configured to enable extension of the joint.

SUMMARY

Exemplary embodiments of an adjustable cut guide and a method of using the adjustable cut guide to guide the path of a cutting tool to resect a bone are disclosed herein. In one embodiment, the adjustable cut guide comprises a guide, a base, an adjustment mechanism and an adjustment member. The guide has an engagement side permitting engagement with portions of the bone, an opposed side spaced from the engagement side, and a guide surface adapted to receive, and guide the path of, the cutting tool. The guide surface extends between the engagement side and the opposed side of the guide. The base has an engagement side permitting engagement with portions of the bone and an opposed side spaced from the engagement side. The base is coupled to the guide. The adjustment mechanism drivingly engages at least one of the guide and the base to adjust a distance separating the guide and the base when the adjustment mechanism is actuated. The adjustment member has an engaged position and a disengaged position and includes a drive end having a cross-section profile for drivingly mating with the adjustment mechanism. The drive end is operably coupled in driving relationship with the adjustment mechanism in the engaged position. The adjustment member traverses the guide surface in the engaged position to actuate the adjustment mechanism and does not traverse the guide surface in the disengaged position.

In another embodiment, the adjustable cut guide comprises a guide, a base, adjustment means for adjusting a distance separating the guide and the base and actuation means for actuating the adjustment means. The guide has an engagement side permitting engagement with portions of the bone, an opposed side spaced from the engagement side, and a guide surface adapted to receive, and guide the path of, the cutting tool. The guide surface extends between the engagement side and the opposed side of the guide. The base has an engagement side permitting engagement with portions of the bone and an opposed side spaced from the engagement side. The base is coupled to the guide. The actuation means has an engaged position and a disengaged position. A portion of the actuation means traverses the guide surface in the engaged position to actuate the adjustment means. The actuation means does not traverse the guide surface in the disengaged position.

An embodiment of the method of guiding the path of the cutting tool to resect a bone comprises several steps including providing a cut guide having a guide, a base, an adjustment mechanism and an adjustment member. The guide has an engagement side permitting engagement with portions of the bone, an opposed side spaced from the engagement side, and a guide surface adapted to receive, and guide the path of, the cutting tool. The guide surface extends between the engagement side and the opposed side of the guide. The base has an engagement side permitting engagement with portions of the bone and an opposed side spaced from the engagement side. The base is coupled to the guide. The adjustment mechanism drivingly engages at least one of the guide and the base to adjust a distance separating the guide and the base when the adjustment mechanism is actuated. The adjustment member has an engaged position and a disengaged position and includes a drive end having a cross-section profile for drivingly mating with the adjustment mechanism. The drive end is operably coupled in driving relationship to the adjustment mechanism in the engaged position. The method further includes the steps of positioning the adjustment member in the engaged position, positioning the cut guide adjacent to the bone, actuating the adjustment member to adjust the position of the guide surface relative to the base, and positioning the adjustment member in the disengaged position. The adjustment member traverses the guide surface in the engaged position to actuate the adjustment mechanism and is removed from the guide surface in the disengaged position.

BRIEF DESCRIPTION OF THE DRAWINGS

The above-mentioned and other features of the disclosure, and the manner of attaining them, will become more apparent and will be better understood by reference to the following description of embodiments of the disclosure taken in conjunction with the accompanying drawings, wherein:

FIGS. 1 and 2 are front side views of an adjustable cut guide according to one disclosed embodiment showing an actuation mechanism in disengaged and engaged positions, respectively;

FIG. 8 is a side view of a boom with an adjustable stylus according to one disclosed embodiment;

FIG. 9 is a side view of a boom with a fixed stylus according to another disclosed embodiment;

Corresponding reference characters indicate corresponding parts throughout the several views. The exemplifications set out herein illustrate embodiments of the application and such exemplifications are not to be construed as limiting the scope of the invention in any manner.

DETAILED DESCRIPTION

Figure 3:
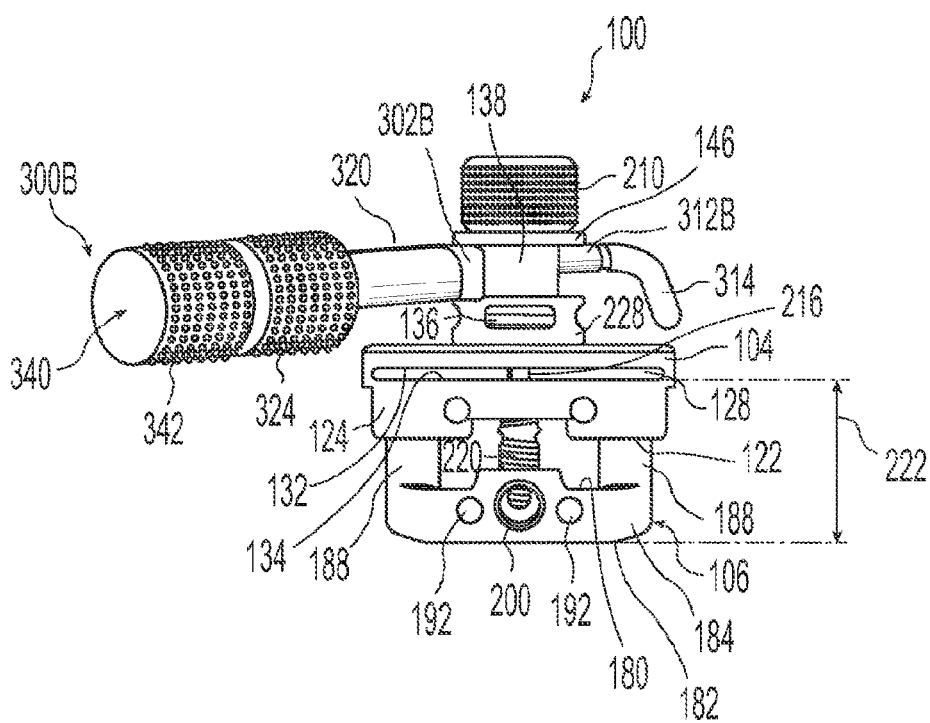
FIG. 3 is a front side view of a boom according to one disclosed embodiment positioned on the adjustable cut guide of FIGS. 1-2.

An improved adjustable cut guide is disclosed herein having a guide surface disposed between an actuation mechanism and the base of the adjustable cut guide. The adjustable cut guide comprises a base adjustably coupled to a guide having a guide surface. The actuation mechanism may be manipulated to adjust the distance between the base and the guide. In operation, the base may be affixed to a bone at a desired position. Once the base has been affixed, the distance between the guide and the base may be adjusted manually to align the guide surface with a desired resection plane without requiring manual access to the front side of the adjustable cut guide. By removing the actuation mechanism from the base of the adjustable cut guide, the size of the base of the adjustable cut guide may be reduced and a greater degree of joint extension may be permissible during the resection procedure.

While the terms anterior and posterior may be used to refer to aspects of a adjustable cut guide in the context of an anterior-posterior adjustable cut guide for convenience, such use does not limit the scope of the present invention. Equivalent terms may include top and bottom, respectively. The side of the adjustable cut guide which engages the bone may be referred to as the engagement or back side, and the side opposite the engagement side may be referred to as the front or opposite side.

Exemplary embodiments of an adjustable cut guide having an actuation mechanism positioned on the top side of the adjustable cut guide and generally designated by the number 100 are disclosed herein. FIGS. 1 and 2 show adjustable cut guide 100 with actuation mechanism 208 disengaged and engaged, respectively. Adjustable cut guide 100 includes guide 104, base 106 and actuation mechanism 208 for adjusting the distance between guide 104 and base 106.

Guide 104 includes cut slot 128 defined by anterior surface 132 and posterior, or guide, surface 134. Guide 104 is slidably coupled to base 106. Guide 104 comprises top side 120 spaced apart from bottom side 122. Top and bottom side 120, 122 extend perpendicularly from front side 124 and back side 126 (shown in FIG. 5). Cut slot 128 connects back side 126 and front side 124. Guide surface 134 extends between back side 126 and front side 124 and is adapted to receive, and guide the path of, a cutting tool. Base 106 comprises top side 180 spaced apart from bottom side 182. Top and bottom side 180, 182 extend perpendicularly from front side 184 and back side 186 (not shown). Cut slot 128 may be disposed at various angles relative to a plane parallel to bottom side 182. In one embodiment, cut slot 128 is parallel to bottom side 182. In another embodiment, cut slot 128 is at a 4° angle relative to bottom side 182 which is orthogonal to engagement side 126, 186 to ensure the cutting instrument does not create a notch on femur 22. In another embodiment, guide 104 includes guide surface 134 but does not include a cut slot.

FIG. 1 shows adjustable cut guide 100 in a partially extended position, which position is described in detail below, with actuation mechanism 208 disengaged. In operation, a compressive force is applied against knob 210 to slide actuation mechanism 208 towards base 106. The compressive force is opposed by tension provided by a biasing means, shown as annular spring 136. Alternative biasing means may include metallic and plastic elastic portions having any of a plurality of shapes including rectangular substantially flat shapes, V-shapes and cube shapes. Actuation mechanism 208 includes an adjustment member, shown as shaft 212 having drive end 216, and may include knurled knob 210. Shaft 212 is connected to knurled knob 210 at the end opposite drive end 216 and may have a circumferential groove 214 disposed between them.

Figure 6A:
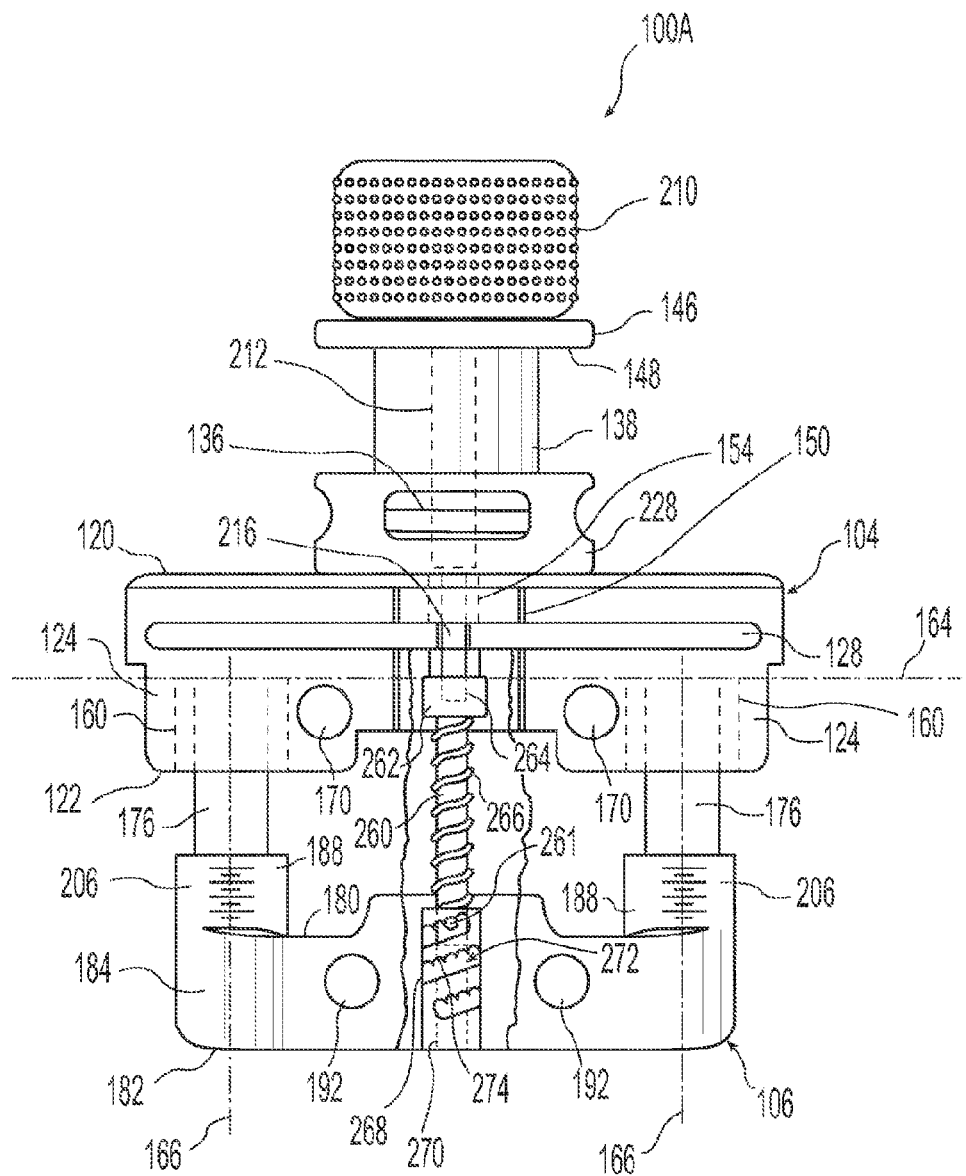
FIGS. 6A and 6B are front side views of embodiments of adjustable cut guides showing alternative adjustment mechanisms.
Figure 6B:
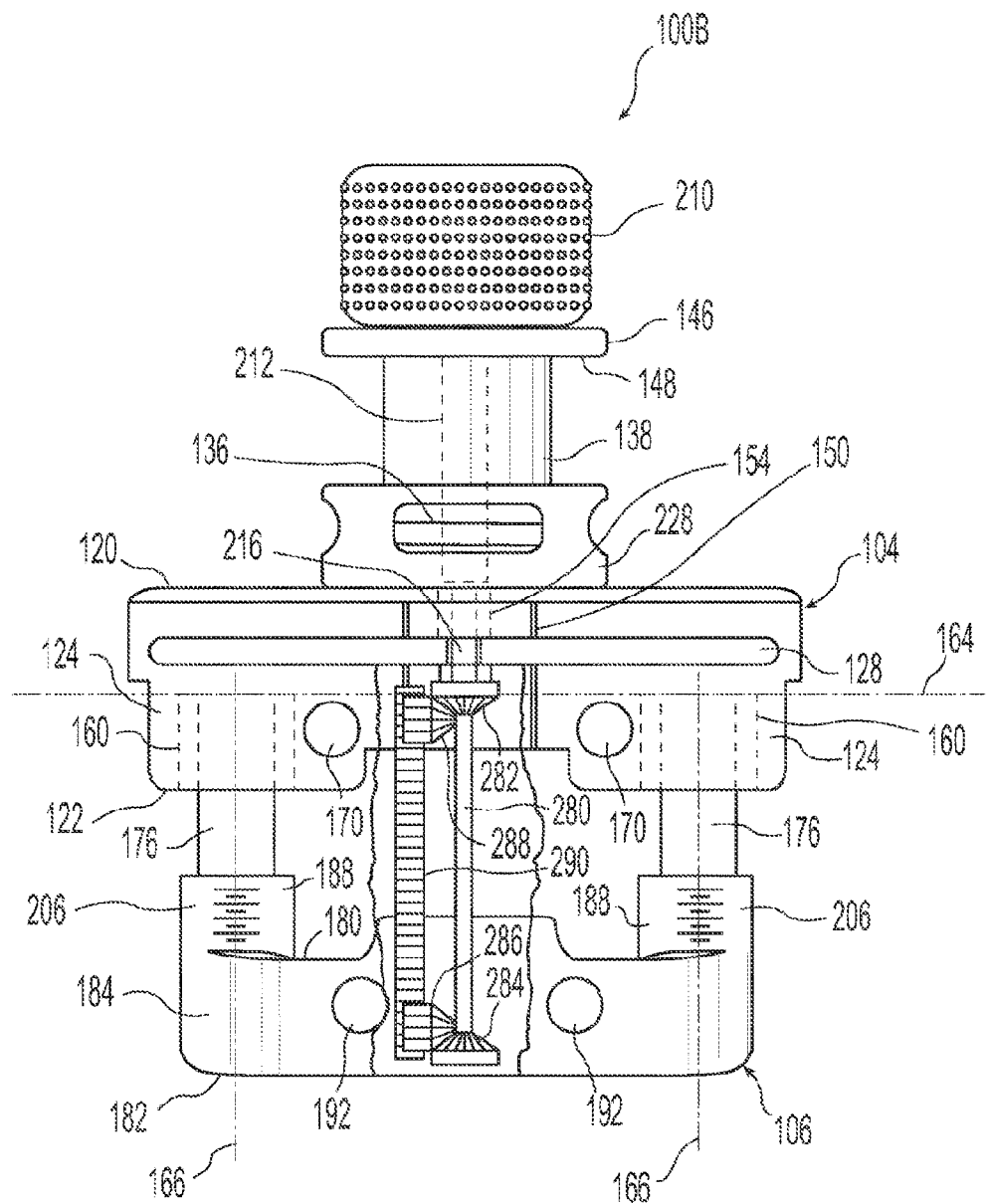

Adjustable cut guide 100 also has an adjustment mechanism threadedly engaging at least one of guide 104 and base 106. The adjustment mechanism adjusts the distance, or A/P height 222, separating guide 104 and base 106 when the adjustment mechanism is actuated. A/P height 222 is the distance between bottom side 182 of base 106 and guide surface 134. The adjustment mechanism mates with drive end 216 of the adjustment member when the adjustment member is engaged at which time the adjustment member traverses guide surface 134. In the embodiment shown, the adjustment mechanism includes threaded rod 220. Alternative embodiments of adjustment mechanisms may comprise worm gears and combinations of helical slots and pins as shown in FIGS. 6A and 6B. FIG. 2 shows adjustable cut guide 100 in a partially extended position with actuation mechanism 208 engaged. FIG. 3 shows actuation mechanism 208 held in the engaged position by boom 300B.

Figure 4:
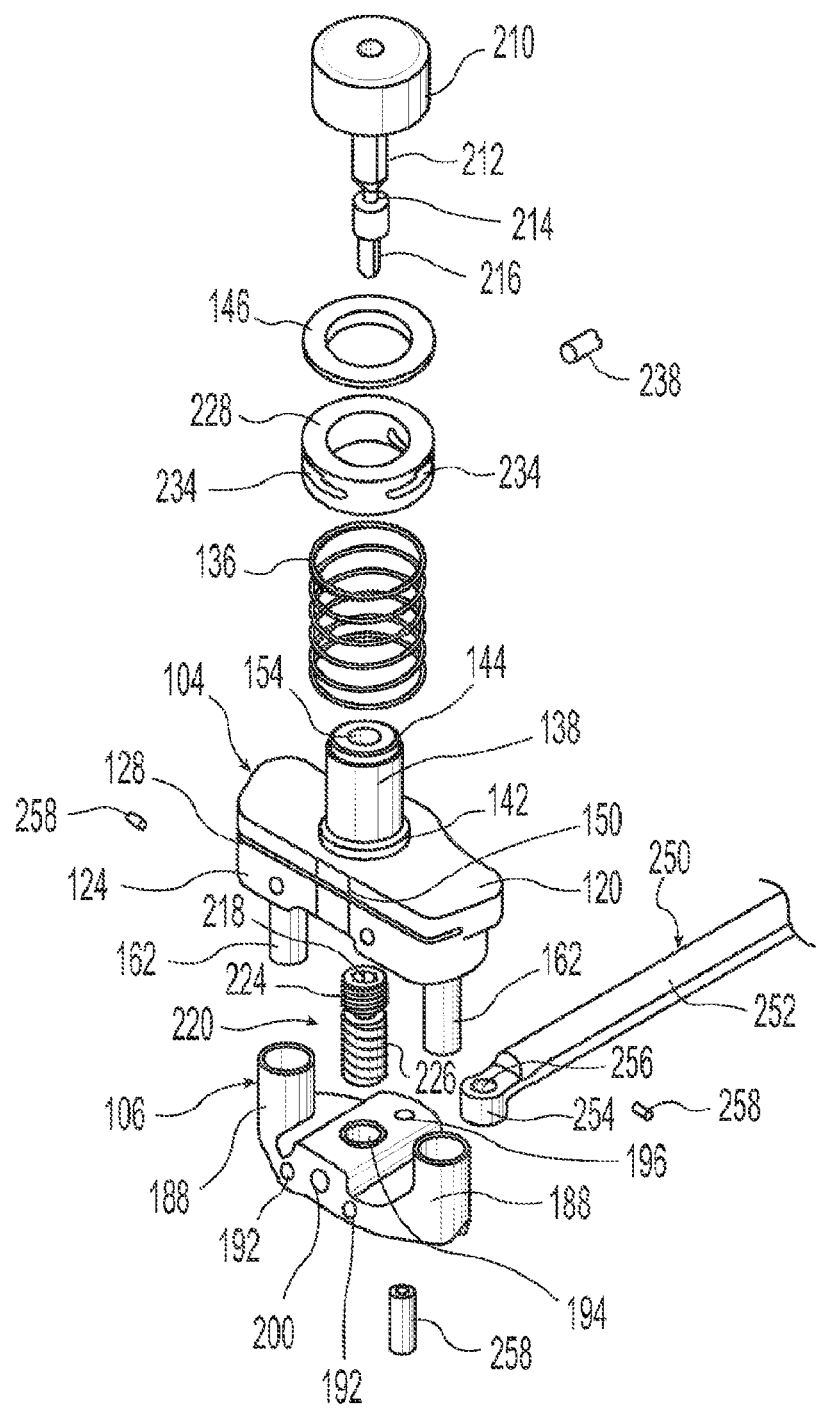
FIG. 4 is an exploded perspective view of the adjustable cut guide of FIGS. 1-2 and an intramedullary guide.
Figure 5:
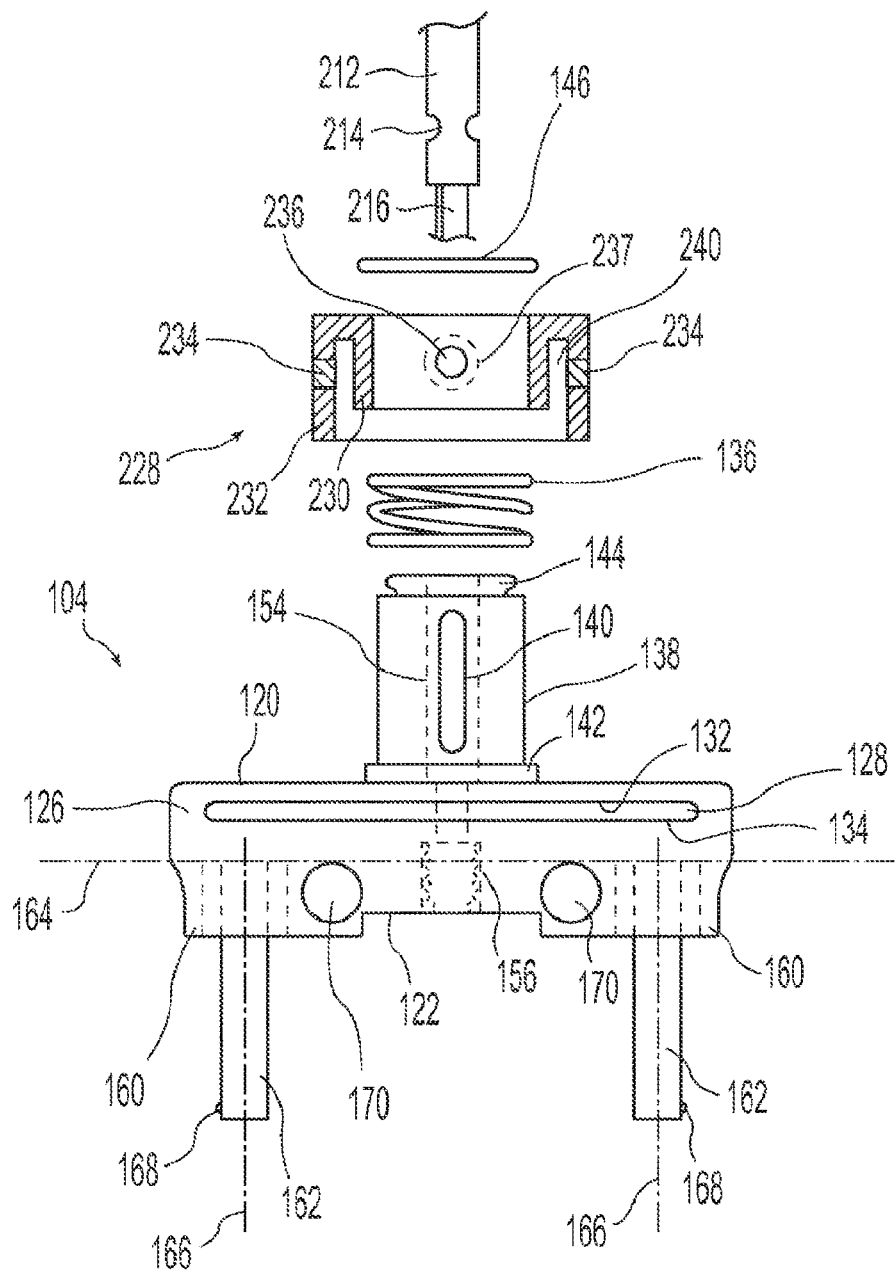
FIG. 5 is an exploded partial rear side view of the adjustable cut guide of FIGS. 1-2.
Figures 10, 11:
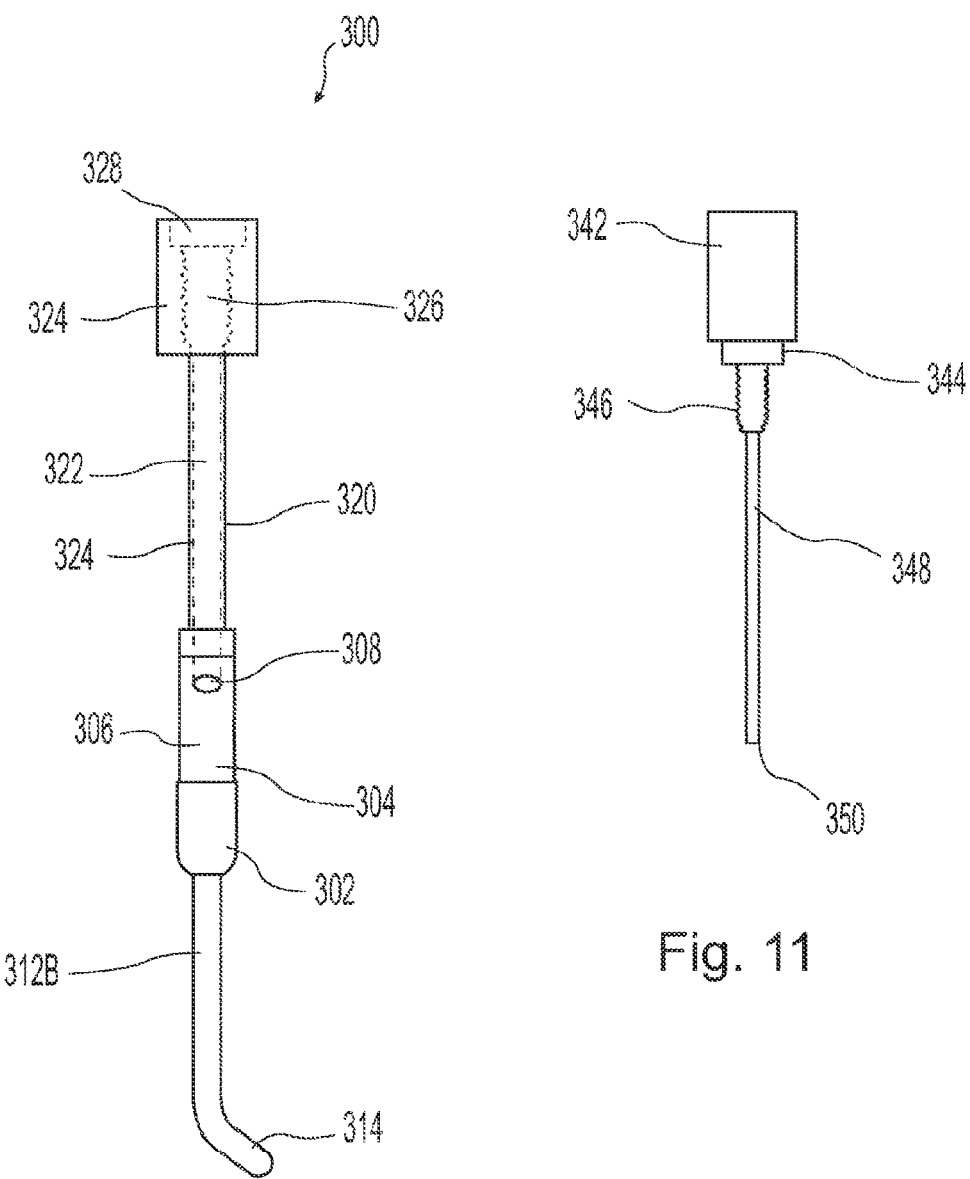
FIGS. 10 and 11 are cross-sectional side views of the boom of FIG. 9.

FIGS. 4 and 5 are exploded perspective views of adjustable cut guide 100. FIG. 4 shows the front side of adjustable cut guide 100. FIG. 5 shows back side 126 of guide 104 and a partial view of actuation mechanism 208. Adjustable cut guide 100 may include a support member adapted to hold actuation mechanism 208 in the engaged position. In the embodiment shown, the support member includes head collar 138 for receiving actuation mechanism 208. Head collar 138 extends from top side 120 and includes slot 140 disposed longitudinally thereon (shown in FIG. 5), neck 144 disposed on one end thereof and lip 142 disposed on the other end. Crown 146 is affixed to neck 144 after biasing means 136 and adjustment collar 228 are positioned on head collar 138. Crown 146 creates flange 148 for retaining adjustment collar 228 on head collar 138. Biasing means 136 may be positioned over lip 142 to reduce friction between the surface of biasing means 136 and the external surface of head collar 138. Biasing means 136 moves actuation mechanism 208 away from guide 104 when actuation mechanism 208 becomes disengaged until head collar 138 contacts flange 148. While actuation mechanism 208 is engaged, head collar 138 is exposed for receiving opening 304 of boom 300B. Boom 300B is shown in detail in FIGS. 9-11. Boom 300B may be coupled to adjustable cut guide 100 by sliding opening 304 onto head collar 138 between crown 146 and adjustment collar 228. Boom 300B may be secured by turning knob 342.

In another embodiment, the adjustment member has an annular collar disposed between drive end 216 and its opposite end and the support member has an elongate aperture through its center sized to receive the adjustment member including the annular collar. The support member is adapted to receive a boom sized and configured to operably couple with the annular collar of the adjustment member to maintain the adjustment member in the engaged position.

Actuation mechanism 208 may comprise adjustment collar 228 having hole 236 and member 238 for rotatably coupling adjustment collar 228 to shaft 212. Exemplary member 238 includes a screw and a pin. Adjustment collar 228 comprises annular slot 240 disposed between internal wall 230 and external wall 232. Three slots 234 are disposed on external wall 232 with their longitudinal dimensions perpendicular to the axis of adjustment collar 228. Hole 236 is disposed on internal wall 230 perpendicularly to the axis of adjustment collar 228. Hole 237 is disposed on external wall 232 for enabling member 238 to pass therethrough. Slots 234 are provided to hold biasing means 136 back while securing member 238 to hole 236. Annular slot 240 receives biasing means 136 when adjustment collar 228 is placed on head collar 138. Shaft 212 penetrates adjustment collar 228 until groove 214 is aligned with threaded hole 236. Member 238 is secured to hole 236 with one end protruding therethrough and through slot 140 into groove 214 to thereby rotatably couple shaft 212 to adjustment collar 228 and prevent rotation of adjustment collar 228 about head collar 138 when knob 210 is rotated. A top-to-bottom directed force applied to knob 210 causes actuation mechanism 208, including adjustment collar 228, to travel from the disengaged to the engaged position. In the engaged position, drive end 216 traverses guide surface 134 while in the disengaged position drive end 216 does not traverse guide surface 134.

Adjustment hole 156 threadedly receives threaded rod 220 for adjusting A/P height 222. Threaded rod 220 has top thread 224 and female key 218 disposed on one end and bottom thread 226 disposed on the opposite end. Top thread 224 has a pitch which is opposite the pitch of bottom thread 226. Top thread 224 engages adjustment hole 156 of guide 104 and bottom thread 226 engages adjustment hole 194 of base 106. In one embodiment, the pitch of bottom thread 226 is greater than the pitch of top thread 224 such that when threaded rod 220 is turned, threaded rod 220 engages (or disengages) base 106 at a faster rate than guide 104. In one embodiment, the pitch of top thread 224 is half the pitch of bottom thread 226. Female key 218 is a recess having a cross-section profile configured to mate female key 218 with drive end 216. Exemplary cross-sectional profile shapes include hexagonal, square, oval, crosshead, Pozidriv, Torx, Allen, Robertson, and pentagonal. When actuation mechanism 208 is engaged, drive end 216 passes through driver hole 154 and couples with female key 218. Knob 210 may then be rotated to rotate threaded rod 220 to adjust A/P height 222. A/P height 222 may be adjusted with and without a boom. In an alternative embodiment, threaded rod 220 has only one thread, is threadedly engaged with one of guide 104 and base 106 and is rotatably coupled to the other of guide 104 and base 106. In another embodiment, one or both of top thread 224 and bottom thread 226 comprise more than one start. Screw starts are the number of independent threads on the screw shaft, for example one, two, or four. The thread lead is the axial distance a mating thread advances in one revolution of the screw and is equal to the pitch times the number of starts. Pitch is equal to lead in a single start screw. In yet another embodiment, drive end 216 has a recess for engaging a male key disposed on the end of threaded rod 220.

Guide 104 also comprises components for guiding its movement relative to base 106. Guide 104 includes guide holes 160 and guide posts 162. Guide holes 160 extend from bottom side 122 to surface 164 and are configured to receive guide collars 188 of base 106. Guide posts 162 extend downwardly from surface 164 along a common centerline 166 with guide holes 160 and guide collars 188. Guide posts 162 are slidably received by guide collars 188 and include protrusions 168 (shown in FIG. 5) for setting the end-of-travel, i.e. maximum A/P height 222, of adjustable cut guide 100. Guide Collars 188 include narrow longitudinal grooves on their inside surfaces (not shown) which slidably receive protrusions 168. Protrusions 168 may be provided in a unitary construction with guide posts 162 or may be affixed to guide posts 162. Selected ones of fixation holes 170 secure guide 104 by means of fixation members (not shown) adapted to pass therethrough and attach to femur 22. Guide 104 may comprise vertical alignment lines 150 on front side 124 for aligning adjustable cut guide 100 with reference marks 116 and 118 (shown in FIGS. 12, 14 and 15).

FIGS. 6A and 6B are front views of cut guides 100A and 100B, respectively, showing in partial cut-outs alternative adjustment mechanisms. FIG. 6A shows rod 260 having collar 262 at one end and pin 261 disposed at the opposite end perpendicularly to the axis of rod 260. Collar 262 has female key 264 for receiving and mating with drive end 216. Base 106 includes collar 268 having slot 272 for receiving pin 261. Slot 272 has helical shape and comprises a multitude of indentations 274 disposed on one side for receiving pin 261. The pitch of the helix and the number of indentations 274 determines the rate of adjustment per turn of rod 260. Spring 266 is disposed on rod 260 between collar 262 and collar 268. Spring 266 provides a biasing force to separate guide 104 and base 106. As rod 260 is rotated, pin 261 drivingly engages collar 268 of base 106 by sliding from one indentation 274 to another to adjust A/P height 222. As guide 104 and base 106 approach, rod 260 may extend through hole 270 of collar 268. In another embodiment, slot 272 is disposed on guide 104.

FIG. 6B shows another embodiment of an adjustment mechanism illustrating a twin bevel gear system drivingly engaging a toothed rack. Rod 280 has gear 282 at one end and gear 284 disposed at the opposite end. Gear 282 engages gear 288. One of gear 282 and rod 260 is configured to receive and mate with drive end 216. Gear 288 engages teeth of rack 290 and moves guide 104 relative to rack 290 along the axis of rack 290 when gear 282 is rotated. Gear 284 engages gear 286. Gear 286 drivingly engages rack 290 and moves base 106 relative to rack 290 along the axis of rack 290 when gear 284 is rotated. Gears 288 and 286 rotate in opposite directions when gears 282 and 284 are rotated by rod 280 thereby cooperating to adjust A/P height 222. An alternative embodiment comprises a worm-gear arrangement. A worm is a threaded rod provided to rotate gears 286 and 288. The worm is configured to receive and mate with drive end 216. Drive end 216 rotates the worm to adjust A/P height 222. In another embodiment, drive end 216 engages bevel gear 282. In one embodiment, only guide 104 is drivingly engaged and rod 280 is not used.

Figure 7A:
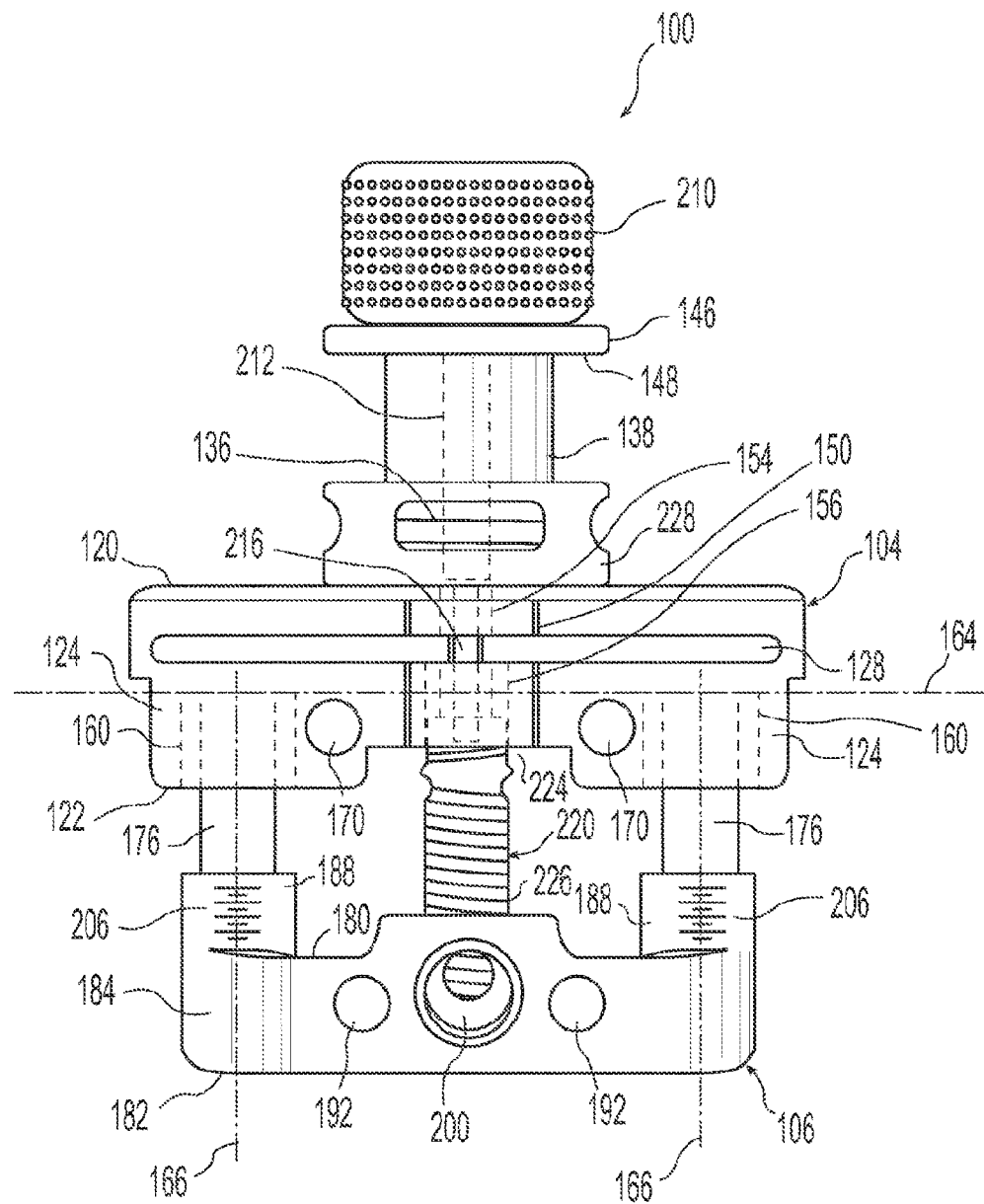
FIGS. 7A and 7B are front side views of the adjustable cut guide of FIGS. 1-2 shown in extended and retracted positions, respectively.
Figure 7B:
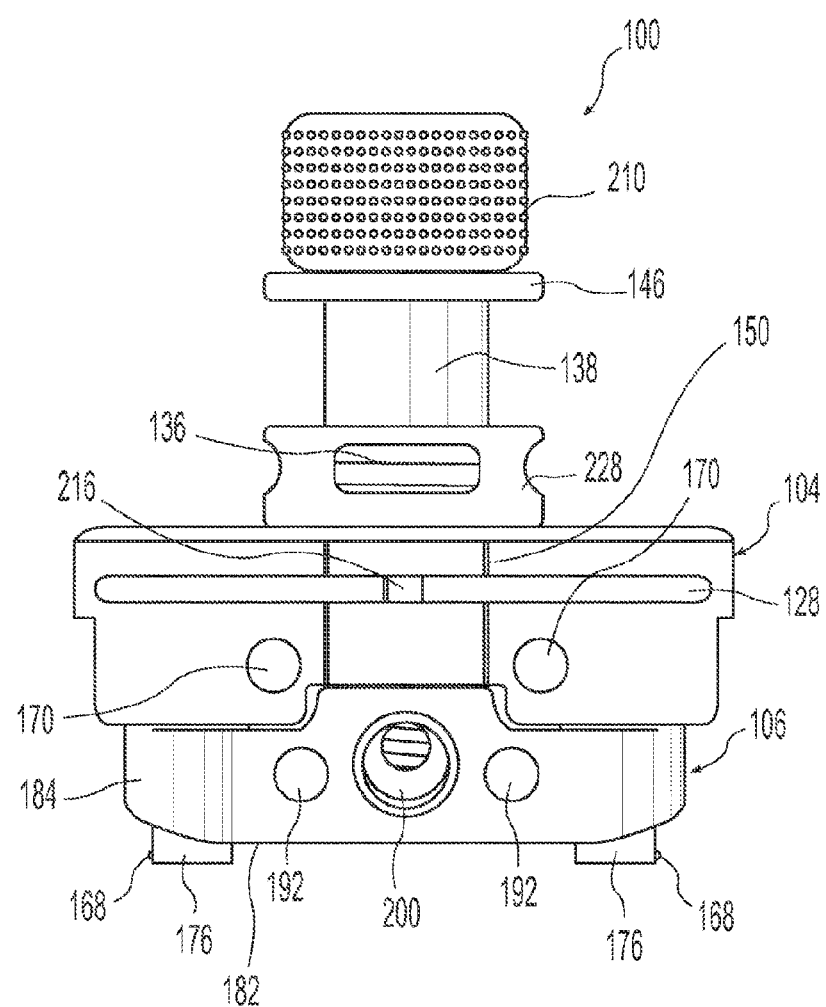

FIGS. 7A and 7B show adjustable cut guide 100 in extended and retracted positions, respectively, with actuation mechanism 208 disengaged. The extended position is reached when protrusions 168 prevent guide 104 from separating further away from base 106. The retracted position is reached when bottom side 122 of guide 104 contacts top side 180 of base 106. FIG. 7B shows guide posts 162 visibly extending through bottom side 182 of base 106 exposing protrusions 168.

A common procedure in knee arthroplasty involves drilling a hole in the intramedullary (IM) canal several inches along the anatomical axis of the femur starting slightly anterior to the intercondylar notch. The anatomical axis extending from the sulcus at the center of the femur between the condyles to the center of the femoral trochanter is at a slight angle, usually 5 to 6 degrees, to the mechanical axis. Following drilling, an IM guide is positioned in the hole along the IM canal and extends outwardly therefrom. The IM guide is used in combination with an adjustable cut guide to direct the cutting instrument along the proper path to be cut.

Referring again to FIG. 4, base 106 includes various holes adapted to align and secure adjustable cut guide 100 to the bone. Hole 196 and recess 198 (not shown) are provided to rotatably couple base 106 to IM guide 250. Recess 198 extends from back side 186 towards adjustment hole 196 and comprises two substantially flat sides parallel to top side 180 and bottom side 182 which define an opening depth. Hole 196 traverses base 106 from top side 180 to bottom side 182 and passes through recess 198. IM guide 250 comprises IM rod 252 opposite IM coupling portion 254. IM coupling portion 254 comprises two parallel substantially flat sides which define a thickness and which are traversed by IM hole 256. IM rod 252 may be coupled to base 106 by inserting IM coupling portion 254 through recess 198 until hole 196 is aligned with IM hole 256. A coupling member 258, e.g., a pin or screw, may be inserted through hole 196 and IM hole 256, and secured to base 106, to enable base 106 to rotate about IM guide 250 in directions which are parallel to the flat sides of IM coupling portion 254. The depth of recess 198 is slightly larger than the thickness of IM coupling portion 254 to substantially limit movement of base 106 relative to IM rod 252 except as provided above. In use, IM rod 252 be inserted in the IM canal to position base 106 in a known relationship to the IM canal based on the design of base 106. Base 106 may comprise fixation holes 192 for securing base 106 to a bone by means of fixation members (not shown) adapted to pass therethrough and attach to the bone.

FIGS. 8-11 show a boom with an adjustable stylus and a boom with a fixed stylus, respectively. Boom 300A comprises base 302A, adjustable stylus 318, and adjustable handle 340. Adjustable stylus 318 has knob 316 for rotating stylus arm 312A to extend or retract stylus tip 314. In one embodiment, stylus arm 312A has threaded portion 313 threadedly engaged with threaded hole 310 of base 302A. Base 302A has recess 304 having surface 306 for receiving head collar 138 and hole 308 for receiving rod 350 of adjustable handle 340. Adjustable handle 340, shown partially in detail in FIGS. 10 and 11, includes shaft 320 having hole 322 disposed therethrough. Shaft 320 is connected to base 302A on one end and to collar 324 on the other. Hole 322 abuts hole 308 of base 302A. Collar 324 has threaded hole 326 and hole 328 disposed therethrough. Adjustable handle 340 further includes plunger 341 comprising threaded portion 346 connected to collar 344 at one end and rod 348 at the other. Collar 344 is connected to knob 342 and is received by hole 328. Rod 348 is received by hole 322, 308. Threaded portion 346 is received by threaded hole 326. In operation, knob 341 is rotated to move rod 348 into or out of hole 308. Knob 326 may be rotated clockwise until collar 344 is seated in hole 328 at which time tip 350 of rod 348 will extend into recess 304. If boom 300A is positioned on adjustable cut guide 100, rotating knob 342 will cause tip 350 to press head collar 138 onto surface 306 of thereby temporarily securing boom 300A to adjustable cut guide 100. Boom 300B is substantially similar in function to boom 300A except that stylus arm 312B is fixed to base 302B.

Following are descriptions of embodiments of a method of using adjustable cut guide 100 in performing surgery on the distal side of a femur. A similar method may be used with adjustable cut guide 100 positioned in obvious fashion to perform surgery on other bones. Such a similar method is within the scope of the present invention.

Figure 12:
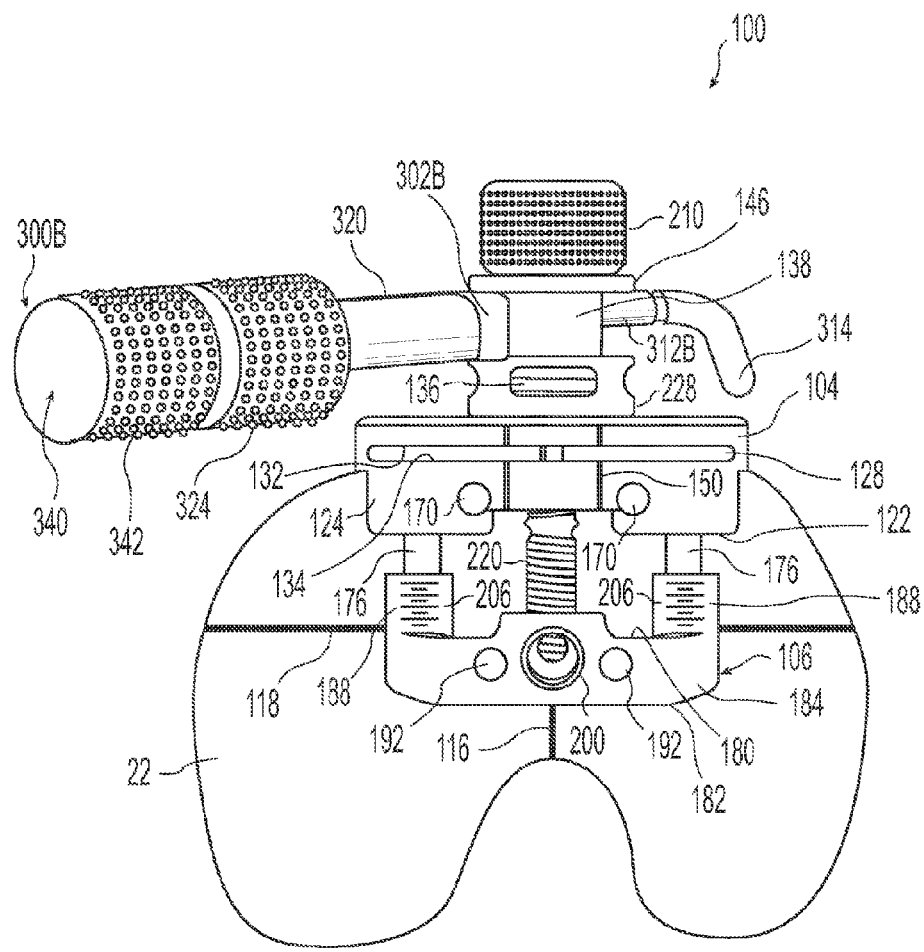
FIG. 12 is a front side view of the adjustable cut guide of FIGS. 1-2 in an extended position with the boom of FIG. 9 positioned on the adjustable cut guide and the adjustable cut guide affixed to a femur.

Referring now to FIG. 12, adjustable cut guide 100 is shown in an extended position at the desired location adjacent the distal end of femur 22 with boom 300B positioned thereon. Optional horizontal alignment lines 206 may be used to align adjustable cut guide 100 with reference line 116, 118. Reference line 118, the A/P axis, is marked from the lowest part of the trochlea to the highest part of the intercondylar notch, and a traverse line 116 that is perpendicular to the A/P axis is also marked. The transepicondylar axis may also be used as reference. Alternatively, reference line 116, 118 may determine the location where femur 100 may be perforated to insert IM rod 252. IM rod 252 is inserted until back side 126 of guide 104 and back side 186 of base 106 engage the distal femoral sulcus. Adjustable cut guide 100 may be inserted by hand or with an inserter/extractor handle (not shown) coupled to hole 200. External rotation may be adjusted by rotating adjustable cut guide 100. Optionally, base 106 may have a series of lines forming scale 206 for ascertaining the depth of the cut. Selected ones of fixation holes 192 may secure guide 104 by means of fixation members (not shown) adapted to pass therethrough and attach to femur 22 as determined by the surgeon.

Figure 13:
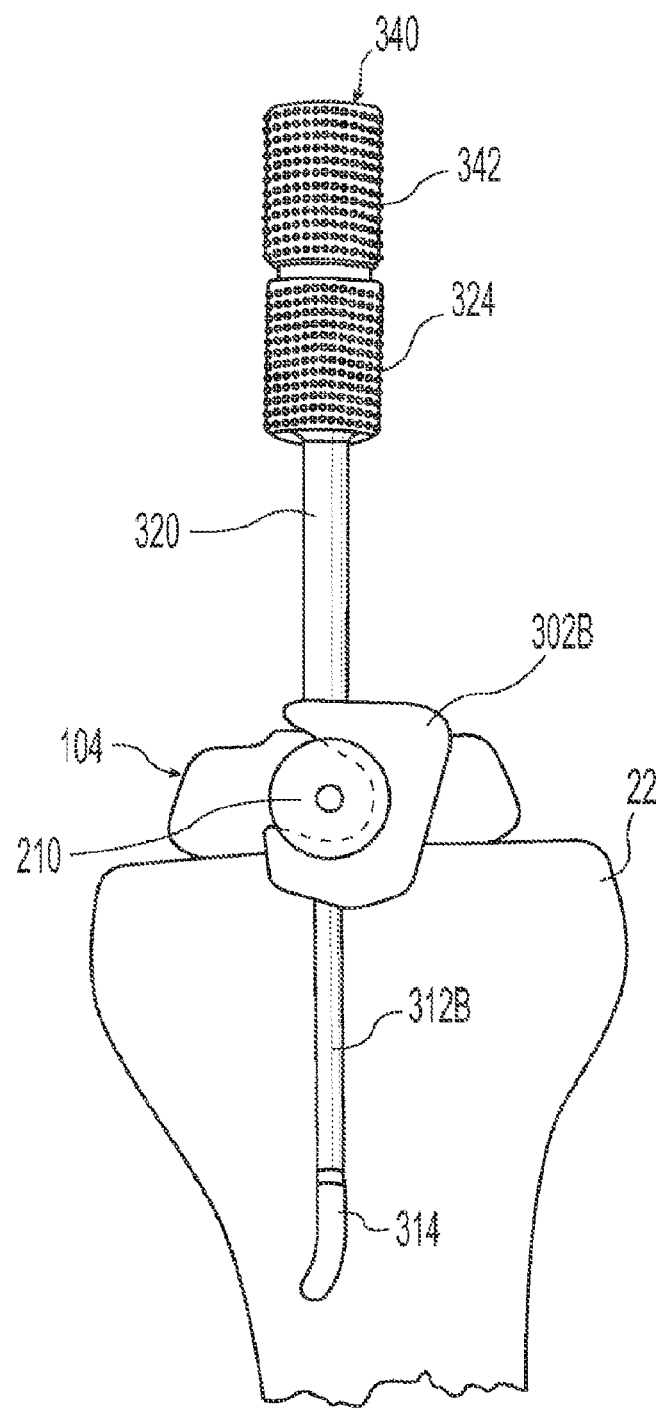
FIG. 13 is a top side view of the adjustable cut guide of FIGS. 1-2 with the boom of FIG. 9 positioned on the adjustable cut guide and the adjustable cut guide affixed to the femur.

FIG. 13 is a top side view of FIG. 12 showing back side 126 of guide 104 engaging the distal end of femur 22. Following affixation of base 106 to femur 22, A/P height 222 may be reduced to create a flush cut with the anterior cortex of femur 22 by turning knob 210 to move guide 104 toward base 106 until stylus 314 engages the lateral facet of the anterior cortex. Stylus 314 may be rotated about head collar 138 to ensure it engages the anterior cortex properly. Optionally, once the proper A/P height 222 has been selected, knob 324 may be rotated to tighten coupling of boom 300B to guide 104 before affixing guide 104 to femur 22. Selected ones of fixation holes 170 may secure guide 104 by means of fixation members (not shown) adapted to pass therethrough and attach to femur 22 as determined by the surgeon.

Figure 14:
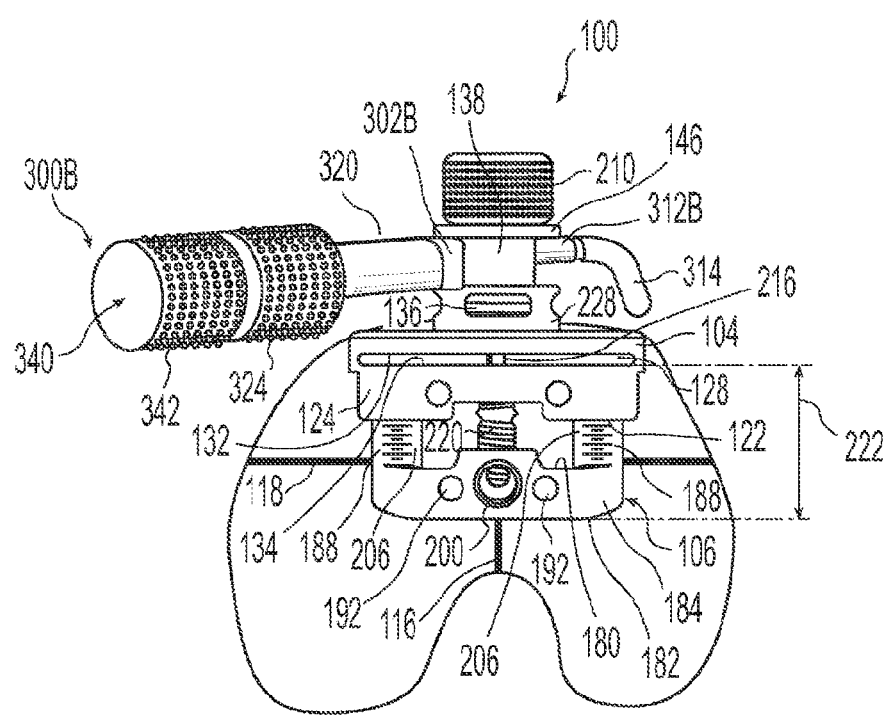
FIG. 14 is a front side view of the adjustable cut guide of FIGS. 1-2 with the boom of FIG. 9 positioned on the adjustable cut guide and the adjustable cut guide affixed to the femur in a partially retracted position.
Figure 15:
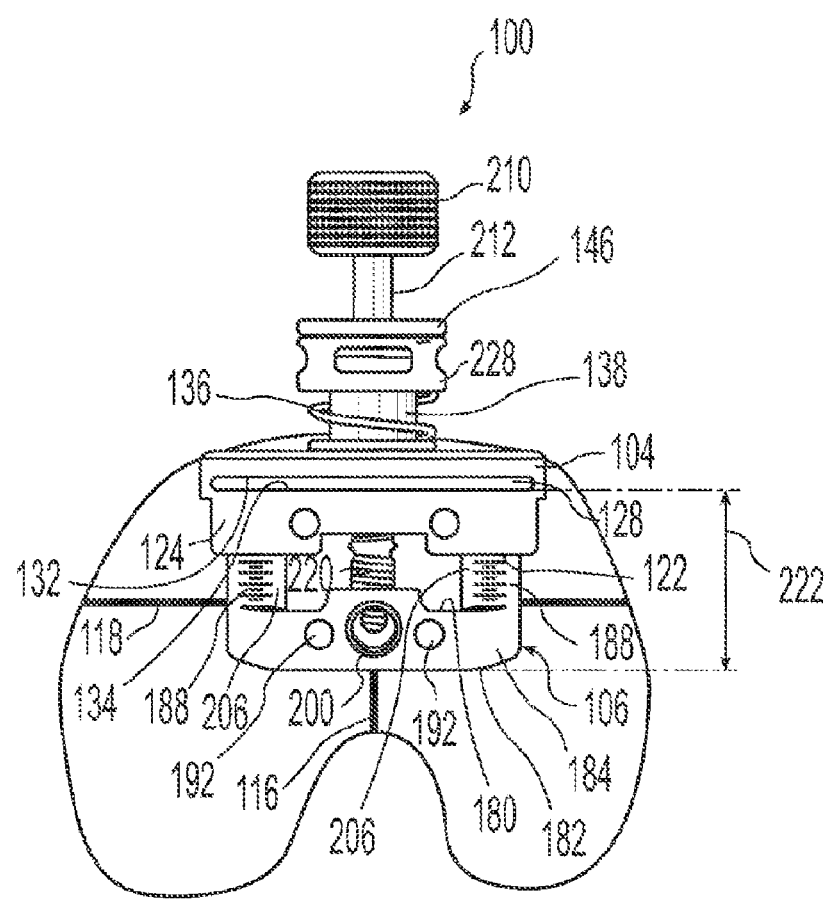
FIG. 15 is front side view of the adjustable cut guide of FIGS. 1-2 without a boom.

FIG. 14 shows adjustable cut guide 100 partially extended after A/P height 222 was reduced. Before resectioning femur 22, boom 300B is removed. Knob 324 may be rotated to loosen coupling of boom 300B to guide 104 and remove boom 300B. Upon removal, actuation mechanism 208 becomes disengaged and drive end 216 retracts from cut slot 128, as shown in FIG. 15, thereby enabling a cutting tool such as a saw blade to pass through cut slot 128 to resect femur 22.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An apparatus for guiding a path of a cutting tool to resect a bone comprising:

a guide having a first engagement side permitting engagement with a portion of a bone, a first opposed side spaced from said first engagement side, and a guide surface adapted to receive, and guide the path of, a cutting tool, said guide surface extending between said first engagement side and said first opposed side;

a base coupled to said guide, said base having a second engagement side permitting engagement with said portion of the bone and a second opposed side spaced from said second engagement side;

an adjustment mechanism drivingly engaging at least one of said guide and said base, said adjustment mechanism adjusting a distance separating said guide and said base when said adjustment mechanism is actuated;

an adjustment member having an engaged position and a disengaged position, said adjustment member including a drive end having a cross-section for drivingly mating with said adjustment mechanism, and said drive end being operably in driving relationship coupled to said adjustment mechanism in said engaged position, wherein said adjustment member transverses said guide surface in said engaged position to actuate said adjustment mechanism, and wherein said adjustment member does not transverse said guide surface in said disengaged position; and a knob disposed at the end of said adjustment member opposite said drive end and a spring disposed between said guide and said knob, wherein said spring is biased to place said adjustment member in said disengaged position.

2. The apparatus of claim 1, further comprising a cut slot having a first surface and a second surface, wherein said first surface comprises said guide surface.

3. The apparatus of claim 1, wherein said drive end cross-section profile is shaped as one of a square, hexagon, star, cross, and triangle.

4. The apparatus of claim 1, further comprising a support member extending from said guide and having an elongate aperture through its center sized for positioning said adjustment member therethrough, said support member being sized to receive a boom supporting a stylus and to hold said adjustment member in said engaged position when said boom is received by said support member.

5. The apparatus of claim 1, wherein said adjustment mechanism includes a rod drivingly engaging at least one of said guide and said base.

6. The apparatus of claim 5, wherein said rod includes a first thread having a first pitch threadedly engaging at least one of said guide and said base to drive one of said guide and said base toward the other.

7. The apparatus of claim 6, wherein said rod further includes a second thread having a second pitch, said first pitch being opposite said second pitch, and said first and second thread threadedly engaging said guide and said base.

8. The apparatus of claim 5, wherein said rod includes a pin protruding radially from one end and said one of said guide and said base includes a helical slot, said pin slidingly engaging said helical slot to drive one of said guide and said base toward the other.

9. The apparatus of claim 1, wherein said adjustment mechanism includes a bevel gear drivingly engaging a toothed rack extending between said guide and said base.

10. An apparatus for guiding a path of a cutting tool to resect a bone comprising:
a guide having a first engagement side permitting engagement with a portion of a bone, a first opposed side spaced from said first engagement side, and a guide surface adapted to receive, and guide the path of, a cutting tool, said guide surface extending between said first engagement side and said first opposed side;
a base coupled to said guide, said base having a second engagement side permitting engagement with said portion of the bone and a second opposed side spaced from said second engagement side;
adjustment means for adjusting a distance separating said guide and said base;
actuation means for actuating said adjustment means, said actuation means having an engaged position and a disengaged position, wherein a portion of said actuation means transverses said guide surface in said engaged position to actuate said adjustment means, and wherein said actuation means does not transverse said guide surface in said disengaged position; and
a biasing means for positioning said actuation means in said disengaged position.

11. The apparatus of claim 10, further comprising a cut slot having a first surface and a second surface, wherein said first surface comprises said guide surface.

12. The apparatus of claim 10, wherein said actuation means has a cross-section profile shaped as one of a square, hexagon, star, cross, and triangle.

13. The apparatus of claim 10, further comprising support means and alignment means, said support means sized to receive said alignment means and to hold said actuation means in said engaged position when said alignment means is received by said support means.

14. The apparatus of claim 10, wherein said adjustment means is drivingly engaged with at least one of said guide and said base.

15. The apparatus of claim 14, wherein said adjustment means is threadedly engaged with at least one of said guide and said base.

16. The apparatus of claim 14, wherein said adjustment means is slidably engaged with at least one of said guide and said base.

17. A method of guiding the path of a cutting tool to resect a bone comprising the steps of:
providing a cut guide including
a guide having a first engagement side permitting engagement with a portion of a bone, a first opposed side spaced from said first engagement side, and a guide surface adapted to receive, and guide the path of, a cutting tool, said guide surface extending between said first engagement side and said first opposed side,
a base coupled to said guide, said base having a second engagement side permitting engagement with said portion of the bone and a second opposed side spaced from said second engagement side,
an adjustment mechanism drivingly engaging at least one of said guide and said base, said adjustment mechanism adjusting a distance separating said guide and said base when said adjustment mechanism is actuated,
an adjustment member having an engaged position and a disengaged position, said adjustment member including a drive end having a cross-section profile for drivingly mating with said adjustment mechanism, and said drive end being operably coupled in driving relationship to said adjustment mechanism in said engaged position,
a support member extending from said guide and having an elongate aperture through its center sized for positioning said adjustment member therethrough, said support member being sized to receive a boom supporting a stylus,
a boom, and
a stylus;
positioning said adjustment member in said engaged position, whereby in said engaged position said adjustment member traverses said guide surface, and holding said adjustment member in said engaged position by positioning said boom on said support member;

positioning said cut guide adjacent to the bone;

actuating said adjustment member to adjust the position of said guide surface relative to said base; and positioning said adjustment member in said disengaged position, whereby in said disengaged position said adjustment member is removed from said guide surface.

18. The method of claim 17, further including, during the actuating step, engaging the bone with said stylus.

19. An apparatus for guiding a path of a cutting tool to resect a bone comprising:

a guide having a first engagement side permitting engagement with a portion of a bone, a first opposed side spaced from said first engagement side, and a guide surface adapted to receive, and guide the path of, a cutting tool, said guide surface extending between said first engagement side and said first opposed side;

a base coupled to said guide, said base having a second engagement side permitting engagement with said portion of the bone and a second opposed side spaced from said second engagement side;

an adjustment mechanism comprising a bevel gear drivingly engaging a toothed rack extending between said guide and said base, said adjustment mechanism adjusting a distance separating said guide and said base when said adjustment mechanism is actuated;

an adjustment member having an engaged position and a disengaged position, said adjustment member including a drive end having a cross-section for drivingly mating with said adjustment mechanism, and said drive end being operably in driving relationship coupled to said adjustment mechanism in said engaged position, wherein said adjustment member transverses said guide surface in said engaged position to actuate said adjustment mechanism, and wherein said adjustment member does not transverse said guide surface in said disengaged position; and a knob disposed at the end of said adjustment member opposite said drive end and a spring disposed between said guide and said knob, wherein said spring is biased to place said adjustment member in said disengaged position.

* * * * *